United States Patent

Malik et al.

[11] Patent Number: 5,523,424
[45] Date of Patent: Jun. 4, 1996

[54] SOLVENT-FREE PROCESS FOR THE SYNTHESIS OF ENERGETIC OXETANE MONOMERS

[75] Inventors: Aslam A. Malik, Cameron Park; Gerald E. Manser, El Dorado Hills; Roland P. Carson; Thomas G. Archibald, both of Fair Oaks, all of Calif.

[73] Assignee: Aerojet-General Corporation, Rancho Cordova, Calif.

[21] Appl. No.: 334,708

[22] Filed: Nov. 4, 1994

[51] Int. Cl.$^6$ .................................................. C07D 305/00
[52] U.S. Cl. .................................................. 549/510
[58] Field of Search ..................................... 549/510

[56] References Cited

U.S. PATENT DOCUMENTS

| | | | |
|---|---|---|---|
| 3,138,609 | 11/1964 | Carpenter | 260/308 |
| 4,102,859 | 7/1978 | Eimers et al. | 260/45.8 A |
| 4,226,777 | 10/1980 | Baum et al. | 260/333 |
| 4,393,199 | 7/1983 | Manser | 528/409 |
| 4,405,762 | 9/1983 | Earl et al. | 525/410 |
| 4,414,384 | 11/1983 | Berkowitz et al. | 528/417 |
| 4,483,978 | 11/1984 | Manser | 528/408 |
| 4,707,540 | 11/1987 | Manser et al. | 528/417 |
| 4,764,586 | 8/1988 | Manser et al. | 149/19.6 |
| 4,804,424 | 2/1989 | Hinshaw | 149/19.6 |
| 4,938,814 | 7/1990 | Schonyer et al. | 149/19.9 |
| 4,952,644 | 8/1990 | Wardle et al. | 525/410 |
| 5,049,214 | 9/1991 | Hassell et al. | 149/109.4 |

FOREIGN PATENT DOCUMENTS

| | | |
|---|---|---|
| 223679 | 11/1968 | Russian Federation . |
| 1112496 | 5/1968 | United Kingdom . |

*Primary Examiner*—C. Warren Ivy
*Assistant Examiner*—Amelia Owens
*Attorney, Agent, or Firm*—Townsend and Townsend and Crew

[57] ABSTRACT

This invention relates to a process for the preparation of mono- and bis(azidomethyl)oxetanes. These compounds are prepared by combining a mono- or bis-X-oxetane (wherein X is, for example, a tosylate, mesylate, halogen, etc.) with an aqueous solution of a metallic azide and a phase transfer catalyst. Mono- and bis(azidomethyl)oxetanes can be polymerized to form homopolymers and copolymers with load bearing polyether backbones and highly energetic pendant groups. Such homopolymers and copolymers of the present invention are useful as energetic binders in high-energy formulations, such as propellants, explosives, and gasifiers.

19 Claims, No Drawings

SOLVENT-FREE PROCESS FOR THE SYNTHESIS OF ENERGETIC OXETANE MONOMERS

FIELD OF THE INVENTION

This invention relates to a process for the preparation of mono- and bis(azidomethyl)oxetanes that is superior to previously known methods. More specifically, 3,3-bis(azidomethyl)oxetane (BAMO) and 3-azidomethyl-3-$R^1$-oxetanes (wherein $R^1$ is, for example, lower alkyl, alkoxy, hydroxy, $NF_2$, $ONO_2$, $NO_2$, etc.) are prepared using the process of the present invention. Such oxetane compounds are useful as ingredients in energetic binders for high-energy formulations, including, for example, propellants, explosives, gasifiers, or the like.

BACKGROUND OF THE INVENTION

High-energy solid formulations, such as propellants, explosives and gasifiers, generally consist of particulate solids, such as fuel material, oxidizers or both, held together by an elastomeric binder. These formulations may also include a liquid plasticizer, such as a nitrate ester, which contributes to the elastomeric characteristics of the binder and adds additional energy to the formulation.

While the elastomeric binder matrix is an important means of dispersing and immobilizing the fuel material and oxidizer, the materials used in the binder burn with substantially lower energy than does the fuel material. The binder thus imposes a limit on the energy content available from the fuel material. One way to minimize this limitation is to use an elastomeric binder which releases as much energy as possible when burning with the fuel material. It is desirable, therefore, that the elastomeric binder have pendant groups which themselves are relatively high in energy.

To this end, 3,3-bis(azidomethyl)oxetane (BAMO) and 3-azidomethyl-3-$R^1$-oxetanes (wherein $R^1$ is, for example, hydrogen, lower alkyl, alkoxy, hydroxy, $NF_2$, $ONO_2$, $NO_2$, etc.) are useful monomers since polyethers prepared from these oxetane compounds can be subsequently cured to form high-energy binder materials. It has been determined that in addition to retaining the necessary characteristics of a binder, such as good elastomeric and mechanical strength properties, polyethers containing mono- and bis(azidomethyl)oxetanes are sufficiently high in energy and sufficiently miscible with nitrate ester plasticizers to be useful as elastomeric binders in propellant formulations and other energetic compositions.

Unfortunately, the use of the energetic azido pendant group in oxetane monomers has been severely limited by economic, environmental and safety considerations. Currently, the reaction of inorganic azides with organic halides to give organic azides, e.g., BAMO, is carried out in dipolar, aprotic solvents such as dimethylformamide (DMF) or dimethylsulfoxide (DMSO). Solutions of sodium azide in DMF and DMSO are, however, hazardous and, thus, are unsuitable for industrial scale reactions. Sodium azide is highly toxic, but when in DMSO or DMF, it is even more hazardous. DMSO and DMF will carry sodium azide into the blood stream and, thus, great care must be taken to avoid contact with such sodium azide solutions. Moreover, sodium azide is not real soluble in DMSO or DMF and, thus, it must be slowly added to such organic solvents while stirring. Unfortunately, sodium azide is very impact sensitive and if, for example, the stirring paddle contacts the solid sodium azide, an explosion can result. In addition, it is extremely difficult to control the pH of such solutions so as to prevent the formation of hydrazoic acid which is highly explosive and toxic. Further, when either DMF or DMSO is used as the solvent, an excess of sodium azide must be used because under the reaction conditions employed, sodium azide gets destroyed. Unfortunately, when energetic materials are used, it is hazardous to open up the reaction system to add additional amounts of sodium azide. Moreover, at the end of the reaction, there is an excess (i.e., about a 10% to 20% excess) of sodium azide which must now be removed. Unfortunately, the removal of excess sodium azide and, in turn, the isolation of the final product from the organic reaction mixture involve multiple steps.

In view of the foregoing, there exists a need for a process for the preparation of 3,3-bis(azidomethyl)oxetane (BAMO) as well as other 3-azidomethyl-3-$R^1$-oxetanes (wherein $R^1$ is, for example, hydrogen, lower alkyl, alkoxy, hydroxy, $NF_2$, $ONO_2$, $NO_2$, etc. ) that overcomes the economic, environmental and safety limitations of the prior art methods. Quite surprisingly, the present invention remedies this need by providing such a process.

SUMMARY OF THE INVENTION

It has now been discovered that mono- and bis(azidomethyl)oxetanes can be readily prepared, without the use of organic solvents (e.g., DMSO and DMF), by combining a mono- or bis-X-oxetane (wherein X is, for example, a tosylate, mesylate, halogen, etc. ) with an aqueous solution of a metallic azide and a phase transfer catalyst. Aqueous solutions of metallic azides (e.g., sodium azide) are easily prepared and are less hazardous to handle and store than azide solutions in organic solvents. Unfortunately, mono- and bis-X-oxetanes (wherein X is, for example, a tosylate, mesylate, halogen, etc.) are immiscible in water and, thus, the rate of any substitution reaction is too slow to be practical even at reflux temperatures. It has been surprisingly discovered, however, that mono- and bis(azidomethyl)oxetanes can be readily prepared, without the use of organic solvents, by using a phase transfer catalyst (PTC) to complex the azide ion and transport it from the aqueous phase into the organic phase. This is true despite the fact that the azide ion is derived from inorganic salts that exhibit poor solubility in organic media, and despite the fact that the rate of such substitution reactions is primarily dependent on the solubility of the reactants in the reaction medium.

As such, in contrast to the prior art, the present invention provides a safe, environmentally sound and cost efficient process for the preparation of energetic oxetane monomers. More particularly, the present invention provides a process for the preparation of energetic monomers that does not utilize an organic solvent as the reaction medium. As such, the process of the present invention avoids the problems associated with the use of organic solvents such as toluene, DMF and DMSO. In particular, the solubility problems, the stability problems, the problems associated with the use of excess sodium azide, the isolation problems, etc. are all avoided by the process of the present invention.

Moreover, the process of the present invention is conducted in an alkaline metallic azide solution and, thus, the formation of hydrazoic acid is suppressed. As mentioned, one of the major problems encountered in the synthesis of organic azides is the formation of hydrazoic acid ($HN_3$) which is highly explosive and toxic. Formation of hydrazoic acid can be avoided by conducting the reaction in a basic medium. Unfortunately, with organic solvents, this is not possible since the presence of the base will promote side reactions such as hydrolysis and elimination. This is, however, possible with the aqueous metallic azide solutions used in the process of the present invention. The pH of aqueous metallic azide solution can readily be controlled so as to prevent the formation of hydrazoic acid.

In addition, the process of the present invention has a built in temperature control which prevents run away reactions from occurring. More particularly, in preferred embodiments, the process of the present invention is conducted at reflux which removes heat from the reaction, thereby avoiding exothermic, run away reactions. In this system, the temperature is controlled by a phase change, i.e., by water changing from the liquid phase to the vapor phase. As the water in the reaction system boils, the water undergoes a phase change from liquid to vapor, the vapor enters the condenser where it is cooled, the vapor undergoes a phase change back to the liquid phase, and the cooled liquid is added back to the reaction system, thereby maintaining the temperature of the reaction system at about 100° C. to about 105° C. As such, by conducting the reaction at reflux, exothermic, run away reactions, which are a serious problem when organic solvents are employed, are avoided.

Other advantages, objects, features and embodiments of the present invention will become apparent from the detailed description which follows.

DETAILED DESCRIPTION OF THE INVENTION AND PREFERRED EMBODIMENTS

In one aspect of the present invention, a process is provided for the preparation of a compound having the formula

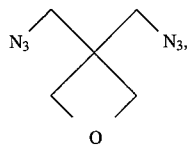

(I)

the process comprising: (a) combining a compound having the formula

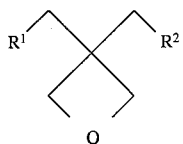

(II)

in which $R^1$ and $R^2$ are independently selected and may be functional groups including, but not limited to, tosylate, mesylate and halogens with an aqueous solution of a metallic azide and a phase transfer catalyst to form a product mixture; and (b) recovering compound I from the product mixture.

The term "independently selected" is used herein to indicate that the two R groups of the compound of Formula II, i.e., $R^1$ and $R^2$, may be identical or different. The term "halogen" is used herein to refer to the nonmetallic elements of the seventh group of the periodic table including, but not limited to, Br, Cl, I and F. The term "tosylate" is used herein to refer to p-toluenesulfonate, i.e., a $CH_3C_6H_5SO_3$—radical. The term "mesylate" is used herein to refer to methylsulfonate, i.e., a $CH_3SO_3$—radical. Within the scope of Formula II, certain embodiments are preferred, namely those in which $R^1$ and $R^2$ are halogens. More particularly, preferred embodiments are those in which $R^1$ and $R^2$ are both Cl, i.e., compound II is 3,3-bis(chloromethyl)oxetane. Equally preferred are embodiments in which $R^1$ and $R^2$ are both Br, i.e., compound II is 3,3-bis(bromomethyl)oxetane.

As used herein, the term "metallic azide" refers to an alkali or alkaline-earth metal azide including, but not limited to, one of the following: sodium azide, lithium azide, aluminum azide, potassium azide, rubidium azide, calcium azide, magnesium azide and barium azide. Certain of these alkali or alkaline-earth metal azides are preferred, namely sodium azide, lithium azide, aluminum azide and potassium azide. More preferred are embodiments wherein the metallic azide is sodium azide.

The term "phase transfer catalyst" is used herein to refer to a compound that can carry or transport the nucleophile, e.g., the azide ion, from the aqueous phase into the organic phase. Suitable phase transfer catalysts include, but are not limited to, the following: quaternary ammonium salts, quaternary phosphonium salts, polyethers and crown ethers. Certain phase transfer catalyst are preferred, namely quaternary ammonium salts including, for example, tetramethyl-and tetra-n-butyl-ammonium bromide, chloride, hydroxide and hydrogen sulfate. Equally preferred phase transfer catalysts are the polyethers such as diethylene glycol, triethylene glycol and other polyethylene glycols.

In carrying out the above process, the metallic azide (e.g., sodium azide) is preferably present in at least about a 5% to about a 10% molar excess, per tosyl, mesyl or halo group, to the mono- or bis-X-oxetane being substituted. As such, if 3,3-bis(chloromethyl)oxetane is the starting material used in the above process, the metallic azide would be present in at least a 10% to about a 20% molar excess to 3,3-bis(chloromethyl)oxetane. Moreover, the aqueous solution of metallic azide used in the process of the present invention is a saturated or nearly saturated solution. More specifically, the aqueous solution of metallic azide is about 20% to 50% metallic azide and, more preferably, about 30% to about 35% metallic azide. In addition, the phase transfer catalyst is present at a concentration ranging from about 0.5 mole % to about 15 mole % and, more preferably, at a concentration ranging from about 0.5 mole % to about 1.5 mole %.

The temperature at which the above reaction is conducted can range from about 90° C. to about 110° C. In a presently preferred embodiment, step (a) is performed at a temperature ranging from about 95° C. to about 105° C. Generally, a compound of Formula II, supra, is combined with an aqueous solution of a metallic azide and a phase transfer catalyst, and the mixture is heated at reflux at a temperature ranging from about 90° C. to about 105° C. until the reaction is complete, generally for about 1 to about 24 hours. 3,3-bis(azidomethyl)oxetane compounds prepared using the process of the present invention are recovered and purified using standard methods and procedures known to and used by those in the art. For example, upon completion, the reaction is cooled to ambient temperature, the phases are separated, and the organic (i.e., lower) phase is filtered through an alumina column to achieve purification. The purified material, i.e., 3,3-bis(azidomethyl)oxetane, can then be directly used as a monomer in subsequent polymerization reactions.

In further preferred embodiments of the above process, a compound of Formula II, supra, is combined with an aqueous solution of a metallic azide, a phase transfer catalyst and a base. Suitable bases include, but not limited to, sodium hydroxide, sodium bicarbonate, sodium carbonate, potassium hydroxide and potassium carbonate. BAMO is stable in the presence of sodium azide, but slowly reacts with hydrazoic acid to form the addition product tris-2,2,2-(azidomethyl)ethanol (see, Equation I, infra). Unfortunately, this side reaction is undesirable because this impurity, i.e., tris-2,2,2-(azidomethyl)ethanol, is more shock sensitive than BAMO and, thus, its presence can sensitize the product. It has been determined, however, that formation of this material can be prevented by the addition of small amounts of a base (e.g., sodium hydroxide, sodium bicarbonate, sodium carbonate, potassium hydroxide, potassium carbonate, etc.) to the reaction mixture. BCMO, for example, does not react with sodium hydroxide, sodium bicarbonate, sodium carbonate, potassium carbonate or potassium hydroxide, and any hydrazoic acid formed during the reaction is immediately neutralized. As such, in a presently preferred embodiment of the above process, sodium hydroxide, sodium bicarbonate, sodium carbonate, potassium carbonate or potassium hydroxide is added to the reaction mixture in step (a) at a concentration ranging from about 0.1 mole % to about 3 mole % in order to neutralize any hydrazoic acid that may be formed.

Equation 1

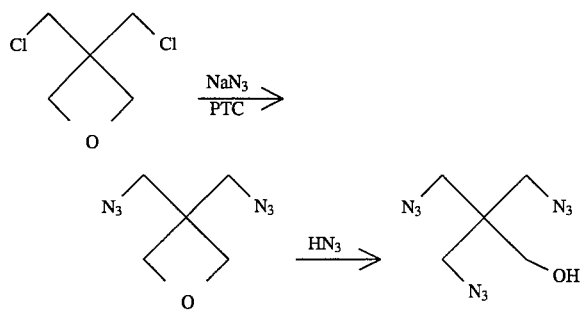

Using the process of the present invention, it has been determined, for example, that in the absence of a phase transfer catalyst, 3,3-bis(chloromethyl)oxetane (BCMO) shows no reaction with aqueous sodium azide at reflux after 3 hours, whereas in the presence of 10 mole-% diethylene glycol, the reaction is 40% complete in 3 hours. Moreover, when 10 mole-% of tetra-n-butylammonium bromide is used, the reaction is 95% complete in 3 hours (see, Table I, infra).

Table I

Relative Rates of Reaction of BCMO with Sodium Azide after 3 Hours

| Mole-% Catalyst | Catalyst | % Completion |
| --- | --- | --- |
| 0 | none | 0 |
| 10 | DEG[a] | 40 |
| 1 | TBAB[b] | 65 |
| 10 | TBAB[b] | 95 |

[a]Diethylene glycol
[b]Tetra-n-butylammonium bromide

In addition, it is known that the reaction of the two chloro groups of BCMO with sodium azide proceeds stepwise through a 3-azidomethyl-3-chloromethyloxetane intermediate (see, Equation II, infra). As such, the effect of PTC concentration for tetra-n-butylammonium bromide on the reaction rate has been studied. In doing so, it has been determined that the rates of displacement of the chloride ions by the azide ion are similar and that the overall reaction rate is dependent on the reaction temperature and on concentration of the PTC (see, Table II, infra). Thus, by controlling the concentration of the PTC, one can, in essence, control the rate of the reaction. Typical safety data for BAMO is shown in Table III, infra.

Equation II

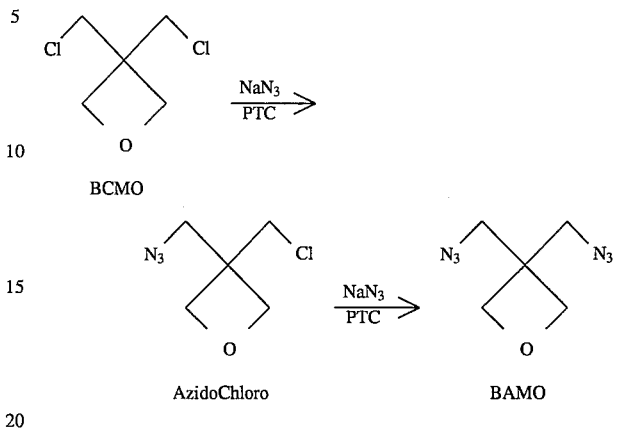

Table II

Effect of TBAB Catalyst Concentration on Products after 3 Hours

| Mole % TBAB | % BAMO | % ChloroAzido | % BCMO |
| --- | --- | --- | --- |
| 10 | 95 | 5 | 0 |
| 2.5 | 94 | 5.5 | 0.5 |
| 1.0 | 63 | 27 | 10 |

TABLE III

BAMO Safety Data

| | BAMO[a] | Reaction Mixture[b] |
| --- | --- | --- |
| Bu/Mines Impact (cm) (50% pt) | >100 | >100 |
| DTA (°F.) onset | 376 | 351 |
| exotherm | 452 | 441 |
| Rotary Friction (gm at 2000 rpm) | >4000 | >4000 |
| Spark (Joules) | >1.0 | >1.0 |
| NOL sleeve test (0 cards) | neg | neg |

[a]Prepared by PTC process
[b]At 50% completion

In another aspect of the present invention, a process is provided for the preparation of a compound having the formula

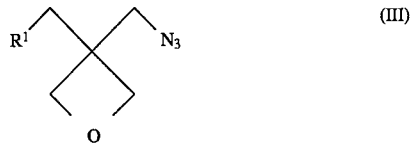

in which $R^1$ is a function group including, but not limited to, H, lower alkyl, alkoxy, OH, $NF_2$, $ONO_2$, $NO_2$ and $N(R^3)NO_2$, where $R^3$ is a lower alkyl, the process comprising: (a) combining a compound having the formula

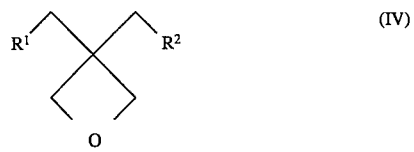

in which $R^2$ is a functional group including, but not limited to, tosyl, mesyl and halogens with an aqueous solution of a metallic azide and a phase transfer catalyst to form a product mixture; and (b) recovering compound III from the product mixture.

In the compounds represented by Formula III, $R^1$ is a functional groups including, but not limited to, H, lower alkyl, alkoxy, OH, $NF_2$, $ONO_2$, NO, $N_3$ and $N(R^3)NO_2$, where $R^3$ is a lower alkyl. The term "alkyl" is used herein to refer to substituents that are monovalent aliphatic hydrocarbon radicals. The alkyl groups may be straight-chain or branched-chain, limited only by steric hinderance. Additionally, since alkyl groups do not add to the energetic character of the molecule, shorter alkyl groups (i.e., 1–4 carbons) and saturated alkyl groups are preferred. The term "alkoxy" is used herein to refer to an alkyl radical which also bears an oxygen substituent that is capable of covalent attachment to another hydrocarbon radical (e.g., a methoxy, ethoxy or phenoxy group). As with alkyl groups, shorter alkoxy groups are generally preferred.

The process for the preparation of 3-azidomethyl-3-$R^1$-oxetanes (wherein $R^1$ is, for example, hydrogen, lower alkyl, alkoxy, hydroxy, $NF_2$, $ONO_2$, $NO_2$, etc.) is similar to the process for the preparation of 3,3-bis(azidomethyl)oxetane except that in step (a), 3-$R^2$-3-$R^1$-oxetane (wherein $R^2$ is, for example, tosylate, mesylate, halogen, etc.) is combined with an aqueous solution of a metallic azide and a phase transfer catalyst. As such, the discussion, definitions, ranges and preferred embodiments pertaining to the process for the preparation of 3,3-bis(azidomethyl)oxetane are fully applicable to the process for the preparation of 3-azidomethyl-3-$R^1$-oxetane with only minor variations.

As such, it has been discovered that monofunctional azidooxetane compounds, i.e., 3-azidomethyl-3-$R^1$-oxetanes, can also be prepared by combining a neat halooxetane with an aqueous metallic azide solution and a phase transfer catalyst (PTC). For example, using the process of the present invention, 3-chloromethyl-3-methyloxetane gives the corresponding 3-azidomethyl-3-methyloxetane (AMMO) in 97% yield. Moreover, 3-bromomethyl-3-hydroxymethyloxetane was previously converted to the corresponding 3-azidomethyl-3-hydroxymethyloxetane in acetone. Using the process of the present invention, however, 3-bromomethyl-3-hydroxymethyloxetane is converted to the corresponding 3-azidomethyl-3-hydroxymethyloxetane, without the use of an organic solvent, using an aqueous sodium azide solution and a phase transfer catalyst. The process of the present invention gives the same result with a faster rate of reaction and without the use of an organic solvent. In addition, 3-chloromethyl-3-methyloxetane 3-chloromethyl-3-phenoxymethyloxetane reacts with an aqueous solution of sodium azide in water with a PTC to give 3-azidomethyl-3-phenoxymethyloxetane in 87% yield.

Other oxetane compounds suitable for use as starting materials in the above process can be synthesized using a variety of different methods. The methods used vary depending upon the oxetane compounds desired. 3-Bromomethyl-3-hydroxy-methyl oxetane (BMHMO), for example, is a convenient and inexpensive route for the preparation of 3,3-asymmetrically disubstituted oxetane compounds. Reaction of 2,2-bis-(bromomethyl) propane-1,3-diol (i.e., neopentyl glycol dibromide) with base catalysts, such as sodium ethoxide in ethanol, gives BMHMO. Additionally, BMHMO can be obtained from the reaction of neopentyl glycol dibromide with sodium hydroxide in dimethylformamide (DMF), sodium hydroxide in dimethylsulfoxide, sodium or potassium hydroxide in ethanol, and by neat reaction with fused potassium hydroxide. Once formed, BMHMO can be used as the starting point for a large number of energetic, asymmetrically disubstituted oxetanes. Oxetanes containing energetic pendant groups such as azido, nitrato, nitro, difluoroamino, nitramino, dinitramino, cubyl and carboranyl can be synthesized using BMHMO as starting material.

Mono- and bis(azidomethyl)oxetanes are particularly useful for polymerizing to form polyethers which may be subsequently cured to form energetic binder materials useful in energetic formulations. U.S. Pat. Nos. 4,393,199, 4,483, 978 and 4,988,797, the teachings of which are incorporated herein by reference, are directed to methods for carrying out cationic polymerization of cyclic ethers to form polymers that can be cross-linked to form elastomeric binders for use in high-energy formulations. Generally, cationic polymerization involves initiation using an adduct, i.e., an initiator, which is a polyhydric alcohol (e.g., a diol, such as 1,4-butanediol) in conjunction with an acid catalyst such as boron trifluoride or an etherate of boron trifluoride. This adduct complexes with a cyclic ether monomer to form an activated cyclic ether. The activated oxetane monomer then reacts with an unactivated oxetane monomer, opening up the oxetane ring and forming a species with a hydroxyl group on one end and an activated oxetane ring on the other end. The activated oxetane ring at the end of the propagating polymer chain reacts further with another unactivated oxetane, and polymerization proceeds in this manner until substantial exhaustion of cyclic ether monomers or, until the reaction is terminated in some other manner.

Using the foregoing teachings, polymerization can be conducted with a single monomer species to form a homopolymer or, with a mixture of monomer species to form a copolymer. The monomers used in the present invention are those which are susceptible to cationic polymerization. Cyclic ethers having three, four, and five membered rings, which are characterized by ring strain, are susceptible to this type of polymerization. In a presently preferred embodiment, oxetane monomers are the cyclic ethers used in the process of the present invention. The oxetane monomers used have the general formula:

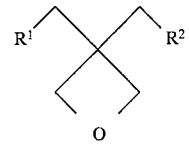

in which $R^1$ and $R^2$ are independently selected and may be functional groups including, but not limited to, H, lower alkyl, $NF_2$, $ONO_2$, $NO_2$, $N_3$, and $N(R^3)NO_2$, where $R^3$ is H or a lower alkyl. Examples of energetic oxetane monomers that can be used to form polymers, either homopolymers or copolymers, with 3,3-bis(azidomethyl)oxetane (BAMO) and the other 3-azidometyl-3-$R^2$-methyloxetanes prepared using the process of the present invention include, but are not limited to, the following: 3-nitratomethyl-3methyloxetane (NMMO); 3,3-bis(methylnitratomethyl)oxetane (BMNAMO); 3-methyl-nitratomethyl- 3-methyloxetane (MNAMMO); 3,3-bis(nitromethyl)oxetane; 3-difluoro-aminomethyl-3-methyloxetane; and 3,3-bis(difluoroaminomethyl)oxetane. It will be understood that "energetic" refers to the energy released by decomposition of the azido, nitro, nitrato and difluoroamino pendant groups. That is to say, apart from heat of combustion an energetic monomer and an energetic polymer have a positive heat of decomposition. It will be further understood that other energetic groups, exemplified by azido, nitro, nitrato and difluoroamino, may also be used.

Any solvent known to be compatible with cationic polymerization with respect to solubility of reactants, stability of the cation formed, etc., may be used. Suitable solvents include, but are not limited to, the following: methylene chloride, Freons, hydrocarbons, chloroform, methyl chloride, ethylene chloride, nitromethane and chlorinated aromatic hydrocarbons, such as, for example, cholorbenzene. In a presently preferred embodiment of the present invention, methylene chloride is the solvent used.

The polymerization reaction is carded out in the absence of any substance which would prevent or prematurely terminate the reaction. Water, for example, should be excluded. The time required to complete or substantially complete polymerization depends upon the reactants and the catalyst used. Polymerization will proceed by chain propagation until substantial exhaustion (e.g., greater than 95%) of the cyclic ether monomers or, until the reaction is terminated in some other manner. The resulting living polymers (i.e., cations) may be terminated in a number of different ways. Termination may be accomplished by adding water to produce terminal hydroxy groups; by adding ammonia or an amine to produce terminal amino groups (e.g., $NH_2$ from ammonia or $-NHCH_3$ from methyl amine); by adding a carboxylic acid or its salt to produce a terminal ester group (e.g., addition of acetic acid produces an acetate group, $CH_3COO-$); or by adding a mineral acid such as HCl, $H_2SO_4$ or HF to produce terminal chlorine, sulfate or fluorine atoms or groups. In general, any terminating species known to terminate living cationic polymers may be used. In a presently preferred embodiment of the present invention, the living polymers are terminated by the alcohol present in the reaction mixture and/or by adding water to produce polymers with terminal hydroxyl groups.

The length of the polymer chains is largely dependent upon the molar equivalents of monomers (m) and the initiators (n), the average chain length being approximately m/n mer units long. Generally, for use in binders, polyether chains are prepared having molecular weights (weight average) of between about 2,000 and about 25,000. It will be readily apparent to those in the art, however, that polyether chains having higher molecular weights (e.g., from 1,000 to about 100,000 (weight average)) can readily be prepared using the method of the present invention. Distribution of mer units throughout the polymer chains and polydispersity of the chains depends upon specific polymerization conditions. Preferably, polyethers have polydispersities between about 1.5 and about 2.0.

If a copolymer is formed, the distribution of mer units derived from Monomer I and mer units derived from Monomer II will depend upon the reactivity ratios of the monomers and upon the proportions in which they are mixed in the charge. If both Monomer I and Monomer II have similar reactivity ratios and if they are charged in roughly equimolar proportions, the resulting polymer will be an atactic polymer having a random distribution of mer units. If, however, Monomer I is more reactive than Monomer II and if Monomer I and Monomer II are charged in equimolar proportions, it can be expected that the head end of the copolymer will predominate in mer units from Monomer I, the tail end in Monomer II, and the mid-portion of the polymer will have a more nearly random distribution of mer units brought about by the fact that the predominance of molecules of Monomer II compensate for its lesser reactivity. As such, the molar ratio of mer units in the polymer formed will depend on both the relative reactivity ratios of the monomers used in the polymerization reaction and the proportions in which they are mixed in the charge.

Preferably, the polymers are hydroxyterminated and, therefore, curable with isocyanates through chain extension and cross-linkable to form elastomers. Polymeric chains which terminate at both ends with primary alcohol groups have a particular advantage since such groups are more reactive toward isocyanate groups during curing than the corresponding secondary and tertiary hydroxyl end groups. Elastomers are formed from the polyethers of the present invention by curing with isocyanates having a functionality of at least two, e.g., toluene diisocyanate. To promote chain elongation, at least one equivalent of an isocyanate is required. Preferably, crosslinking is also promoted by using an isocyanate of higher functionality or, by adding a separate cross-linking agent, such as, for example, trimethylolethane or trimethylolpropane.

The invention will be described in greater detail by way of specific examples. The following examples are offered for illustrative purposes, and are intended neither to limit the invention in any manner.

EXAMPLE I

This example illustrates the preparation and properties of 3,3-bis(azidomethyl)oxetane (BAMO).

A 12 L flask equipped with mechanical stirring and a water-cooled condenser was charged with a solution of sodium azide (1270 g, 19.53 mol) and sodium hydroxide (28 g of a 50% aqueous solution) in water (3.8 L). Then, 3,3-bis(chloromethyl)oxetane (1400 g, 9.03 mol) and tetra-n-butylammonium bromide (63 g, 0.196 mol) were added and the biphasic mixture was heated at about 96° C. to about 103° C. for 24 h. The mixture was cooled to ambient temperature, and gas chromatographic analysis of the separated organic layer indicated that the reaction had reached completion. The organic layer was washed with water (3×1 L) and dried ($MgSO_4$) to give 1445 g of a yellow oil containing tetrabutylammonium salts. The neat oil was passed through a column containing aluminum oxide (400 g), and the column was rinsed with methylene chloride. The solvent was evaporated to give 1313 g (87% yield) of 3,3-bis(azidomethyl)oxetane (>99.5% purity by glc and NMR analysis). NMR: $^1$H NMR: δ3.66 (s, 4H); 4.37 (s, 4H); $^3$C NMR: δ43.417, 54.25, 76.29; glc Rt=5.92 min.

EXAMPLE II

This example illustrates the preparation and properties of 3-azidomethyl-3methyloxetane (AMMO).

A mixture of 3-chloromethyl-3-methyloxetane (10.1 g, 83.5 mmol), tetra-n-butylammonium bromide (0.308 g, 0.96 mmol), sodium azide (6.5 g, 100 mmol) and water (27 mL) was heated at about 96° C. to about 103° C. for 4.5 h, after which time gas chromatographic analysis of the mixture indicated that the reaction had reached completion. The mixture was cooled to ambient temperature, and extracted with methylene chloride (25 mL). The organic extract was passed through a column containing aluminum oxide (10 g), and the column was rinsed with additional methylene chloride. The solvent was evaporated to give 9.84 g (93% yield) of 3-azidomethyl-3methyloxetane (>99.5% purity by glc and NMR analysis). NMR: $^1$H NMR: δ1.32 (s, 3H), 3.52 (s, 2H), 4.25 & 4.35 (AB, J=6.0 Hz, 4H); $^{13}$C NMR: δ21.44, 58.33, 40.03, 79.76; glc Rt=3.19 min.

EXAMPLE III

This example illustrates the preparation and properties of 3-azidomethyl-3-phenoxymethyloxetane.

A mixture of 3-chloromethyl-3-phenoxymethyloxetane (20.0 g, 44 mmol), sodium azide (7.35 g, 113 mmol), sodium bicarbonate (0.53 g, 6.3 mmol), tetra-n-butylammonium bromide (0.653 g, 2.0 mmol) and water (41 mL) was heated at about 109° C. to about 113° C. for 16 h. The mixture was cooled and separated. The organic layer was washed with brine solution, diluted with methylene chloride and filtered through a pad of alumina. The solvent was evaporated to give 17.9 g (87%) of 3-azidomethyl-3-phenoxymethyloxetane as an oil that was pure by glc and NMR analysis. NMR: $^1$H NMR: d 3.71 (s, 2H), 4.07 (s, 2H), 4.42 & 4.46 (AB, J=6.2 Hz, 4H), 6.83–7.21(m, 5H); $^{13}$C NMR: d 43.36,53.88, 68.84, 76.18, 114.47, 121.31, 129.50, 158.45; glc Rt=8.13 min.

EXAMPLE IV

This example illustrates the preparation and properties of 3-azidomethyl-3hydroxymethyloxetane.

A solution of sodium azide (2.07 g, 0.0317 mol), 3-bromomethyl-3-hydroxymethyloxetane (5.0 g, 0.028 mol) and tetra-n-butylammonium bromide (0.0978 g, 0.3 mmol) in water (14 mL) was heated for 3 h at 104°–107° C. The solution was cooled and was extracted with ethyl ether (5×20 mL). The combined extracts were evaporated to give 1.92 g (49%) of 3-azidomethyl-3-hydroxymethyloxetane, essentially pure by glc analysis, as an oil. NMR: $^1$H NMR: 3.70 (s, 2H), 3.84 (d, J=4.9 Hz, 2H), 4.44 (s, 4H); $^{13}$C NMR: 44.283, 53.852, 64.073, 76.227.

EXAMPLE V

This example illustrates the large scale preparation of BAMO. Using the process of the present invention and the procedure which follows, about 40 kilograms of BAMO can be prepared per day. In this example, 3,3-bis(azidomethyl)oxetane (BAMO) is prepared by reaction of 3,3-bis(chloromethyl)oxetane (BCMO) with sodium azide in refluxing water. A phase-transfer catalyst, tetra-n-butylammonium bromide, is employed to accelerate the reaction rate in this heterogeneous reaction system. Upon completion, the reaction is cooled to ambient temperature, phases separated, and the organic (lower) phase filtered through an alumina column to achieve purification. This material is then directly used as monomer in subsequent polymerization reactions.

A 50-gal., Teflon-lined Pfaudler reactor was charged with a solution of sodium azide (36.94 Kg, 568 moles) and tetra-n-butylammonium bromide (1.2 Kg, 3.73 moles) in pH adjusted distilled water (29 gal.). The pH of the solution was >10. The agitator was turned on and the reactor was heated to 215° F. Next, BCMO (36.5 Kg, 235 moles) was added via a pump at a rate 0.264 lb/min. The rate of addition was adjusted to maintain the condenser outlet temperature below 150° F. The progress of the reaction was monitored by glc analysis by following the disappearance of BCMO. On completion, the reactor was cooled to 100° F. by switching from steam to cooling water. After cooling the reaction mixture to 100° F., the agitator was turned off and the reactor was vented. The reaction mixture separates into two layers over a period of 30 mins. The layers were separated and the water layer was transferred to the azide abatement reactor. The organic layer was pumped back into the reactor and washed with pH adjusted water. Again, the layers were separated and the water layer was transferred to the azide abatement reactor. The crude BAMO was then passed through a column filled with alumina (15.4 Kg) at a rate of 0 to 12 gph to give 37 Kg of pure BAMO. The purity of BAMO was determined by glc and NMR analysis and was found to be in excess of 99%. The product was collected in a properly marked drum and stored for future use. This final product can be directly used as a monomer in subsequent polymerization reactions.

The foregoing is offered for purposes of illustration. It will be readily apparent to those skilled in the art that the operating conditions, materials, procedural steps and other parameters of the processes described herein may be furthered modified or substituted in various ways without departing from the spirit and scope of the invention.

What is claimed is:

1. A process for the preparation of a compound having the formula

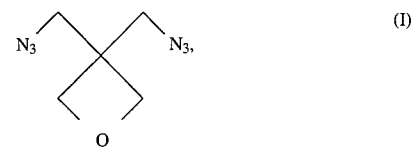

said process comprising:

(a) combining a compound having the formula

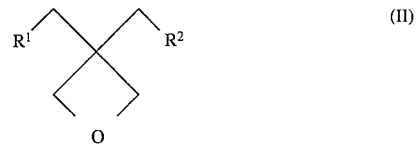

in which $R^1$ and $R^2$ are members independently selected from the group consisting of tosylate, mesylate and halogens with an aqueous solution of a metallic azide and a phase transfer catalyst to form a product mixture; and (b) recovering compound I from said product mixture.

2. A process in accordance with claim 1 wherein $R^1$ and $R^2$ are halogens.

3. A process in accordance with claim 2 wherein $R^1$ and $R^2$ are both Cl.

4. A process in accordance with claim 2 wherein $R^1$ and $R^2$ are both Br.

5. A process in accordance with claim 1 wherein said aqueous solution of said metallic azide is an aqueous solution of sodium azide.

6. A process in accordance with claim 5 wherein said aqueous solution of sodium azide is about 20% to about 50% sodium azide.

7. A process in accordance with claim 1 wherein said phase transfer catalyst is a member selected from the group consisting of quaternary ammonium salts, quaternary phosphonium salts, polyethers and crown ethers.

8. A process in accordance with claim 7 wherein said phase transfer catalyst is a quaternary ammonium salt selected from the group consisting of tetramethylammonium halides and tetra-n-butylammonium halides.

9. A process in accordance with claim 1 wherein step (a) is carried out at a temperature ranging from about 90° C. to about 110° C.

10. A process in accordance with claim 1 wherein step (a) further comprises the addition of a member selected from the group consisting of sodium hydroxide, sodium bicarbonate, sodium carbonate, potassium hydroxide and potassium carbonate.

11. A process for the preparation of a compound having the formula

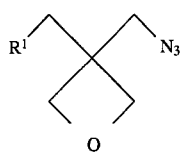

in which R¹ is a member selected from the group consisting of H, lower alkyl, alkoxy, OH, $NF_2$, $ONO_2$, $NO_2$, said process comprising:

(a) combining a compound having the formula

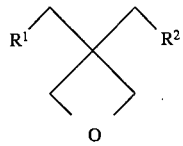

in which R² is a member selected from the group consisting of mesylate, tosylate and halogens with an aqueous solution of a metallic azide and a phase transfer catalyst to form a product mixture; and (b) recovering compound III from said product mixture.

12. A process in accordance with claim 11 wherein R² is a halogen.

13. A process in accordance with claim 12 wherein R² is Cl.

14. A process in accordance with claim 12 wherein R² is Br.

15. A process in accordance with claim 11 wherein said aqueous solution of said metallic azide is an aqueous solution of sodium azide.

16. A process in accordance with claim 15 wherein said aqueous solution of sodium azide is about 20% to about 50% sodium azide.

17. A process in accordance with claim 11 wherein said phase transfer catalyst is a member selected from the group consisting of quaternary ammonium salts, quaternary phosphonium salts, polyethers and crown ethers.

18. A process in accordance with claim 17 wherein said phase transfer catalyst is a quaternary ammonium salt selected from the group consisting of tetramethylammonium halides and tetra-n-butyl-ammonium halides.

19. A process in accordance with claim 11 wherein step (a) further comprises the addition of a member selected from the group consisting of sodium hydroxide, sodium bicarbonate, sodium carbonate, potassium hydroxide and potassium carbonate.

* * * * *